US011391007B2

(12) United States Patent
Benz Navarrete et al.

(10) Patent No.: US 11,391,007 B2
(45) Date of Patent: Jul. 19, 2022

(54) MEASURING DEVICE AND SYSTEM FOR THE GEOMECHANICAL CHARACTERIZATION OF A SOIL, AND CORRESPONDING MEASURING METHOD

(71) Applicant: SOL SOLUTION, Riom (FR)

(72) Inventors: Miguel Benz Navarrete, Clermont-Ferrand (FR); Sébastien Barbier, Clermont-Ferrand (FR)

(73) Assignee: SOL SOLUTION, Riom (FR)

( * ) Notice: Subject to any disclaimer, the term of this patent is extended or adjusted under 35 U.S.C. 154(b) by 0 days.

(21) Appl. No.: 17/167,544

(22) Filed: Feb. 4, 2021

(65) Prior Publication Data
US 2021/0238819 A1     Aug. 5, 2021

(30) Foreign Application Priority Data

Feb. 5, 2020 (FR) ........................................ 2001137

(51) Int. Cl.
*E02D 1/02* (2006.01)
*G01N 3/48* (2006.01)
*G01N 33/24* (2006.01)

(52) U.S. Cl.
CPC ............... *E02D 1/022* (2013.01); *G01N 3/48* (2013.01); *G01N 33/24* (2013.01)

(58) Field of Classification Search
CPC ........... E02D 1/022; G01N 3/48; G01N 33/24
USPC ................................... 73/84, 78, 81, 82, 784
See application file for complete search history.

(56) References Cited

U.S. PATENT DOCUMENTS

| 5,313,825 | A | 5/1994 | Webster et al. |
| 2007/0131025 | A1 | 6/2007 | Kinast et al. |
| 2007/0277598 | A1 | 12/2007 | Zacny et al. |
| 2016/0108598 | A1 * | 4/2016 | Waxse ...................... E02D 7/06 173/46 |

FOREIGN PATENT DOCUMENTS

| CN | 106885747 | * | 6/2017 |
| CN | 110512586 | * | 11/2019 |
| EP | 2944725 | * | 11/2015 |
| JP | H06-317510 | | 11/1994 |
| JP | H10-266718 | | 10/1998 |

(Continued)

OTHER PUBLICATIONS

Search Report for FR2001137 dated Oct. 26, 2020, 2 pages.

*Primary Examiner* — Robert R Raevis
(74) *Attorney, Agent, or Firm* — Nixon & Vanderhye (57) ABSTRACT

A measuring device for geomechanical characterization of a soil, the measuring device including a housing, a dynamic penetrometer, a power supply battery, accommodated in the housing, and an electronic system accommodated in the housing and connected to the battery. The electronic system comprises an accelerometer, as well as a distance sensor, which, in use, is oriented towards a soil and which is adapted to determine the distance between the measuring device and the soil surface by measuring the time required for a wave to travel back and forth between the distance sensor and the soil surface. The electronic system also comprises a processing unit which, when the battery powers the entire electronic system, is adapted to apply processing to measuring signals coming from the accelerometer and the distance sensor.

14 Claims, 7 Drawing Sheets

(56) References Cited

FOREIGN PATENT DOCUMENTS

| JP | H11-241332 | | 9/1999 |
|---|---|---|---|
| JP | 2018-091028 | | 6/2018 |
| KR | 20170035757 | * | 3/2017 |

* cited by examiner

MEASURING DEVICE AND SYSTEM FOR THE GEOMECHANICAL CHARACTERIZATION OF A SOIL, AND CORRESPONDING MEASURING METHOD

This application claims priority to FR Patent Application No. 2001137 filed Feb. 5, 2020, the entire contents of which are hereby incorporated by reference.

The present invention relates to a measuring device for geomechanical characterization of soil. The invention also relates to a measuring system for geomechanical characterization of soil, comprising such a measuring device. It also relates to a measuring method for geomechanical characterization of soil.

BACKGROUND OF THE INVENTION

In civil engineering, the dimensioning of foundations and of any ground structure, such as roadways, foundation layers, embankments, earthworks, etc., requires geotechnical investigations to evaluate the physical and mechanical characteristics of the soil in place. These investigations are often carried out using dynamic penetrometers. These dynamic penetrometers are mainly used to define the soil stratigraphy and to evaluate the bearing capacity of the soils. In some cases, dynamic penetrometers are also used to control the compaction of ground structures. More generally, dynamic penetrometers are used to collect data useful for the geomechanical characterization of soils.

A dynamic penetrometer is a tool used to evaluate the resistance that the soil provides against the boring, by ramming, of a train of rods provided, at its lower end, with a point. Ramming is carried out using a hammer that is raised and then dropped multiple times from a constant height. The operator counts the number of impacts required to drive the point every "X" centimeters into the soil. This distance of "X" centimeters is either chalked on the rods or marked by machining directly on the rods. Since the rods often have a fixed length and the conventional depths of investigation in geotechnics are much greater than this fixed length, the operator must systematically add additional rods to the train of rods to increase the depth of penetration of the train of rods into the soil. At the end of boring, the measuring made by the operator make it possible to evaluate the resistance provided by the soil to penetration according to the depth, in increments of "X" centimeters.

Generally, a dynamic penetrometer comprises a train of rods with a typically conical point at its lower end, a hammer mounted on a guide, and an anvil that receives successive impacts applied by the hammer and transmits them to the train of rods in order to drive the point into the soil. The hammer has a fixed weight and is often in the form of a solid cylinder, which is slidably mounted along a guide bar and may have handles to facilitate lifting the hammer during boring. Due to their relatively simple design and operation, there is now a wide variety of dynamic penetrometers available worldwide. In Europe, the recommendations for use and geometries for dynamic penetrometers are provided by the ISO 2246-2 standard. In the United States, as well as in many countries of the American continent, Asia and Africa, dynamic penetrometers are more likely to meet the American ASTM-D6951-18 2015 standard. In all cases, these different dynamic penetrometers come in different sizes and according to the level of the ramming force, directly related to the weight of the hammer: The use of light dynamic penetrometers, for which the hammer typically weighs eight or ten kilos, is widespread due to their small size and ease of transport, making it possible to characterize a soil for the first five to seven meters of depth, while heavy dynamic penetrometers, for which the hammer can weigh fifty kilos, require larger means of transport and installation.

In the field, the operating mode for boring achieved using such a dynamic penetrometer is the same, regardless of the type of dynamic penetrometer used. It involves driving the tip of the train of rods into the soil, by ramming with the hammer that is raised to a fixed height with respect to the anvil and then released by the operator at different times. During these operations, the number of impacts required to drive the point a distance of "X" centimeters into the soil is counted. Once the point has been driven "X" centimeters into the soil, the number of impacts required to drive the point "X" centimeters further into the soil is counted again. These operations are repeated several times until the end of the boring. In practice, when the dynamic penetrometer has no related measuring instrumentation, these operations are performed by at least two operators, namely a first operator who holds the penetrometer with one hand and raises and drops the hammer from the fixed height with the other hand, and a second operator who counts and notes the number of impacts required to drive the point "X" centimeters into the soil, using the marks on the train of rods as a reference. The boring stops either when the desired boring depth is reached or when opposition is encountered. In general, opposition occurs when the driving force provided by the hammer is insufficient to make the point penetrate into the soil, for example, in case of too much lateral friction between the train of rods and the soil. Boring is also interrupted when the tilt of the train of rods in relation to the vertical is too high, typically more than 10°. At the end of boring, the measurements taken by the second operator permit a posteriori, that is, after the measurements have been processed with ad hoc software, the evaluation of the resistance to the penetration provided by the soil according to the depth and in "X" centimeter increments. The accuracy and reliability of the measurements taken using this procedure, which is very widespread at present, depend on the expertise of the operators, but also on the homogeneity of the soil.

A difficulty or limitation related to the use of dynamic penetrometers concerns the ramming force provided by the impact of the hammer during boring. Since it is not possible to vary the drop height and the weight of the hammer, it is said that the ramming force remains constant. Therefore, depending on the penetrometer used, the ramming force may be either insufficient to penetrate soils of very hard consistency, which entails the rejection and premature termination of the boring, or too high for soft soil evaluation, which entails major boring and a significant dispersion in the measurements. Given that, in nature, the differences in the nature but also in the hardness of soil layers can be frequent, operators are forced either to stop boring and declare the rejection thereof, or to accept measurement inaccuracies.

Faced with this problem, various technical proposals have been made in the past.

U.S. Pat. No. 5,313,825 thus proposed a dynamic penetrometer whose hammer comprises two distinct elements, which are slidably mounted on the same guide and which can be reversibly secured to each other. The operator either uses only one of the two elements to apply impact, with the other element then being released from the penetrometer, or the two elements together after fastening them to each other with dedicated screws. The weight of the hammer can thus be modified depending on whether only one or both elements are used. To remove or add the second element opposite the first element of the hammer, the operator must stop boring, unscrew the screws, typically using a special wrench, and then add or remove the second element. Boring can then be resumed. These operations are time-consuming and tedious. In addition, in the field, there is a high risk of losing the screws and/or the wrench. In addition, increasing or decreasing the weight of the hammer implies an operational precaution that must not be forgotten by the operator in charge of taking measurements: as explained in U.S. Pat. No. 5,313,825, the measurements are taken manually and the operator must therefore indicate, in his follow-up boring, which hammer element(s) is (are) used. Otherwise, subsequent interpretations of the measurements may be distorted, ultimately leading to errors in the calculation of the foundations for the structures projected in the field.

To facilitate the boring measurement after each impact, it is common practice to use graduated rulers, placed vertically parallel to the train of rods, which makes it possible to record the boring obtained after impact. In most cases, these readings are taken by an operator, which requires reading time but also further processing. To overcome this difficulty, systems using analog magnetic rules have also been developed: these systems automate measurement, but they are cumbersome and lack precision in the case of steep soil in which boring is very shallow at each impact. Moreover, the use of these rulers requires a specific mounting on the dynamic penetrometer, increasing the volume of the device and the implementation time.

For its part, US 2007/0131025 proposed the use of a measurement housing, which is equipped with a distance sensor emitting a wave and which is placed on the ground, in the immediate vicinity of the train of rods. A target, such as a cylindrical plate, must be fixed on the penetrometer, typically at the anvil, in order to reflect the wave sent by the distance sensor. The distance sensor thus makes it possible to measure the iterative boring of the train of rods, due to the progressive approach of the target to the soil on which the measurement housing rests. The measurement housing is connected to a separate processing device, such as a computer or a smart phone, in order to know the distance measured by the distance sensor and to follow its iterative decrease as the impacts occur. The housing contains an electric battery, which powers the distance sensor and electronics for the connection to the processing device, but the battery life is limited since the distance sensor operates continuously. In order to relate the iterative decrease of distance measured by the distance sensor to the succession of impacts applied by the hammer, a second sensor, independent of the measurement housing, must be provided on the dynamic penetrometer, this second sensor being sensitive to the presence of the hammer when the latter is lifted at the top of the guide. The measurements from the second sensor are also sent to the processing device so that the latter correlates them to the measurements coming from the distance sensor. The measuring system of US 2007/0131025 is thus complex and not well adapted to the difficult conditions in the field, due to its different separate components and their limited energy autonomy. Moreover, despite saving time taking measurements, the operator needs to perform many preliminary operations for the implementation of this measuring device each time an additional rod is added to the penetrometer. Indeed, each time a new rod is added, before continuing the test, the operator must disassemble the target from the train of rods, connect the new rod and then reposition and adjust the target against the train of rods.

SUMMARY OF THE INVENTION

The object of the present invention is to provide a new measuring device, which is more practical and more efficient.

For this purpose, the invention has as its object a measuring device for the geomechanical characterization of a soil, comprising:
- a housing which is adapted to be secured to a dynamic penetrometer,
- a power supply battery, which is accommodated in the housing, and
- an electronic system, which is accommodated in the housing, which is connected to the power supply battery, and which comprises:
  - an accelerometer adapted to measure an acceleration of the measuring device,
  - a distance sensor, which is oriented towards a soil when the housing is secured to the dynamic penetrometer and which is adapted to determine a distance between the measuring device and a surface of the soil by measuring the time required for a wave emitted by the distance sensor to travel back and forth between the distance sensor and the surface of the soil, and
  - a processing unit, which is connected to the accelerometer and the distance sensor and which, when the electronic system is in an operating state in which the power supply battery powers entirely the electronic system, is adapted to apply a first processing to measuring signals coming from the accelerometer and the distance sensor The invention also has as its object a measuring device for the geomechanical characterization of soil, comprising:
- a dynamic penetrometer, comprising a train of rods, designed to be driven into the soil, and an anvil, designed to receive successive impacts and transmit them to the train of rods, and
- a measuring device, which is as defined above and which is secured to the dynamic penetrometer, in particular to the anvil.

One of the ideas underlying the invention is to arrange, in a housing of the measuring device, an electronic system comprising a distance sensor and an accelerometer, this housing being designed to be attached and secured, by any appropriate means, to a dynamic penetrometer, in particular but not exclusively to the anvil of this dynamic penetrometer. The distance sensor is designed to emit a wave, typically optical or sound, in the direction of the soil against which this wave is reflected to return to the distance sensor: by measuring the time required for the wave to make the round trip between the distance sensor and the soil, the distance sensor makes it possible to determine the distance between it and the surface of the soil, in other words the distance between the measuring device and the surface of the soil. The accelerometer, for its part, provides a measurement signal that shows the acceleration of the measuring device: at each impact applied to the anvil and, through it, to the train of rods, the acceleration of the measuring device shows a peak amplitude. The use of this measurement signal advantageously enables the detection of the different successive impacts and thus the counting thereof, while associating them with a boring of the train of rods into the soil, calculated from the distances measured by the distance sensor at the end of each impact. In practice, the measuring signals coming from the accelerometer and the distance sensor respectively are processed by a processing unit of the electronic system of the measuring device, in order to provide data, the processing of which, in order to detect and thus count the successive impacts and to determine the corresponding progressive boring of the train of rods, can be carried out by this processing unit and/or by an ad hoc processing device, which is separate from the measuring device and the dynamic penetrometer and which, if necessary, is connected wirelessly to the processing unit. This processing device is for example a computer, tablet, smart phone, computer platform, etc., which is separate from the measuring device and the dynamic penetrometer and which, where applicable, is wirelessly connected to the processing unit. In all cases, the measuring device according to the invention provides reliable and precise data for the geomechanical characterization of the soil, while being particularly practical to use, simply by attaching its housing to the dynamic penetrometer while ensuring that the distance sensor is oriented towards the soil since the latter serves as a fixed reference, and this in particular without using other components to be attached to the dynamic penetrometer.

In addition, as detailed below, the use of the measurement signal from the accelerometer advantageously enables the practicality of the measuring device to be reinforced, in connection with its energy autonomy or with the use of a hammer of variable weight. Also as detailed below, the measuring device according to the invention advantageously presents structural arrangements in connection with its housing, or even additional arrangements of the electronic system, thus reinforcing the performance of the measuring device.

Thus, according to advantageous optional features of the measuring device and measuring system according to the invention:

the processing unit is also adapted to:
    switch the electronic system from a standby state, in which the processing unit interrupts the power supply to the distance sensor by the power supply battery, to the operating state when an amplitude of the acceleration measured by the accelerometer exceeds a predetermined threshold, and
    switch the electronic system from the operating state to the standby state when the amplitude of the acceleration measured by the accelerometer remains below said threshold for a predetermined time.
  The measuring device further comprises at least one damper, which is interposed between the housing and the dynamic penetrometer when the housing is secured to the dynamic penetrometer and/or which is interposed between the housing and the electronic system.
  The measuring device further comprises a fastening adapted to secure the housing to the dynamic penetrometer by a reversible mechanical connection and/or by a magnetic connection.
  The electronic system also comprises a tilt sensor, which is connected to the processing unit and which is adapted to measure a tilt of the measuring device relative to the vertical.
  The processing unit of the measuring device is adapted, via the first processing, to detect individually the successive impacts from the measuring signals coming from the accelerometer and to determine boring of the train of rods into the soil after each impact from the measuring signals from the distance sensor.
  The measuring device further comprises a processing device, which is separate from the dynamic penetrometer and the measuring device and which is adapted to apply a second processing to data which result from the first processing applied by the processing unit of the measuring device to measuring signals from the accelerometer and the distance sensor during impacts, and the processing unit and the processing device are adapted, via the first and second processes, to detect individually the successive impacts coming from the measuring signals coming from the accelerometer and to determine boring of the train of rods into the soil after each impact from the measuring signals coming from the distance sensor.
  The dynamic penetrometer also comprises a hammer that (i) is movably mounted on a guide attached to the anvil between a high position, in which the hammer is moved away from the anvil, and a low position, in which the hammer is in contact with the anvil, so that the hammer applies an impact to the anvil when the hammer passes from the high position to the low position, and (ii) includes several separate hammer elements, at least one of which is removable from the rest of the dynamic penetrometer. Furthermore, either the processing unit of the measuring device or the processing unit and the processing device are adapted, via, respectively, either the first treatment or the first and second treatments, to determine which of said hammer elements is or are actually present in the hammer at each impact, from the measuring signals coming from the accelerometer.
  The or each hammer element of the hammer, which is removable relative to the rest of the dynamic penetrometer, is screwable directly onto another hammer element of the hammer.
  The dynamic penetrometer has a mechanical connection adapter between the anvil and the train of rods, whose mechanical connection adapter has:
    on a first side, a first bearing face for the anvil and an internal thread for receiving a threaded end of the train of rods, the internal thread opening to the first bearing face, and
    on a second side opposite the first side, a second bearing face for the anvil and a bore for receiving a smooth cylindrical end of the train of rods, the bore opening onto the second bearing face.

The invention also relates to a measuring method for the geomechanical characterization of soil,
wherein the measuring method uses:
  a dynamic penetrometer comprising a train of rods, designed to be driven into the soil, and an anvil, designed to receive successive impacts and transmit them to the train of rods, and
  a measuring device, which is as defined above and which is secured to the dynamic penetrometer, in particular to the anvil,
and wherein the measuring method comprises the steps of:
  measuring an acceleration of the measuring device upon each impact, using the accelerometer,
  detecting individually the successive impacts from the measured accelerations, by processing them by the processing unit,
  measuring a distance between the measuring device and the soil after each impact, using the distance sensor, and
  determining boring of the train of rods into the soil after each impact from the measured distances, by processing them with the processing unit.

This measuring method can be implemented by the measuring device and measuring system, as defined above.

According to an optional advantageous aspect of the measuring method according to the invention, the dynamic penetrometer further comprises a hammer, which is movably mounted on a guide attached to the anvil, which is used to apply each impact to the anvil by raising the hammer to a predetermined height from the anvil and then releasing the hammer to fall on the anvil, and which includes several separate hammer elements, at least one of which is removable from the rest of the dynamic penetrometer. Furthermore, the measuring method also comprises a step of determining which of said hammer elements is or are actually present in the hammer at each impact, from the measured acceleration upon the impact.

BRIEF DESCRIPTION OF THE DRAWINGS

The invention will be better understood by reading the following description, given only as an example and made with reference to the drawings in which.

DETAILED DESCRIPTION OF THE PREFERRED EMBODIMENTS

Figure 1:
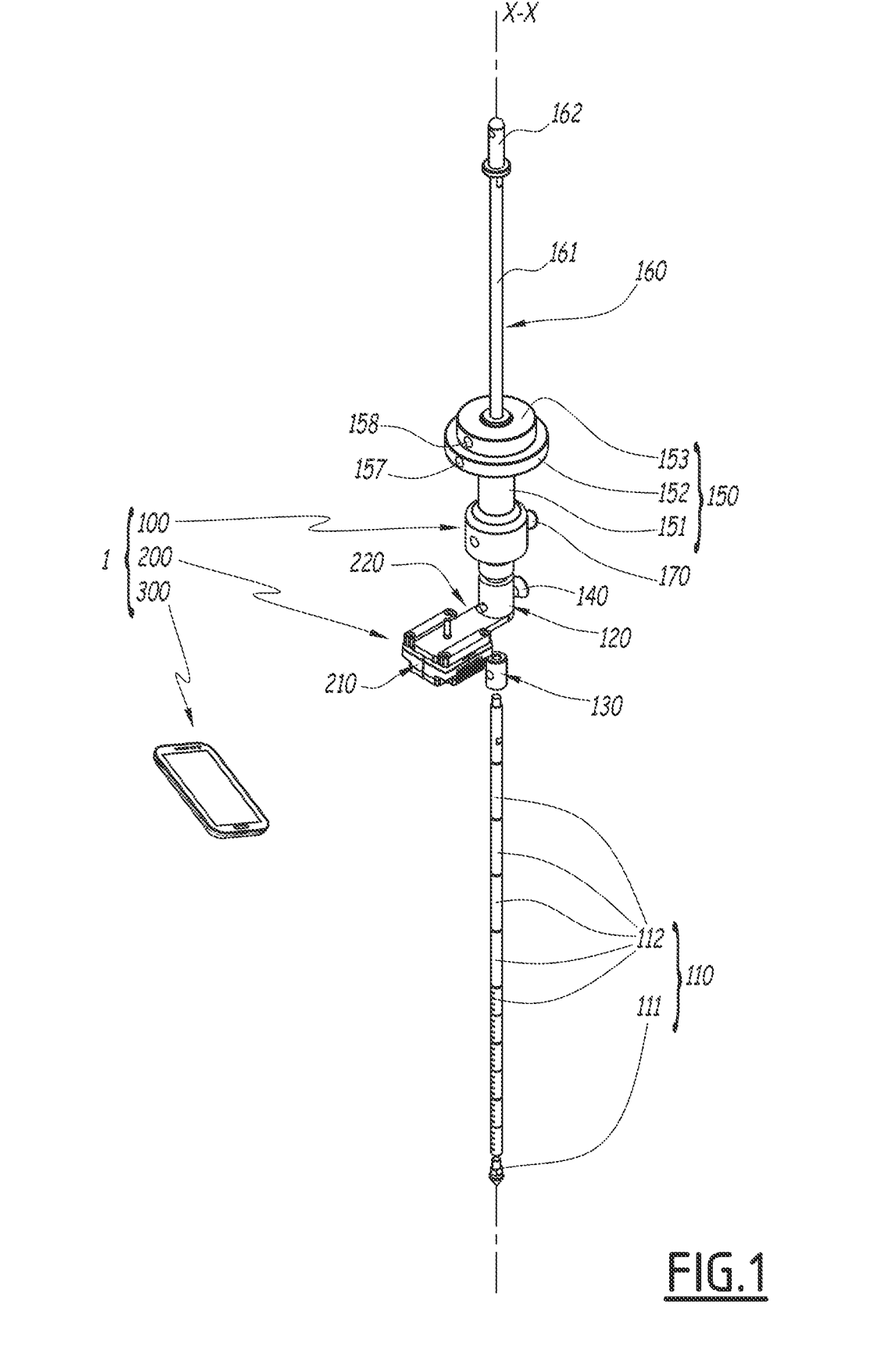
FIG. 1 is an expanded perspective view of a measuring system according to the invention.

FIGS. 1 to 7 show a measuring system 1 for measuring the geomechanical characteristics of a soil. In FIG. 1, the measuring system 1 is shown in a non-functional configuration, while in FIGS. 6 and 7, the measuring system 1 is shown in use on a soil 2 of a terrain whose physico-mechanical characteristics are being evaluated. In FIGS. 2 to 5, only part of the measuring system 1 is shown.

Figure 6:
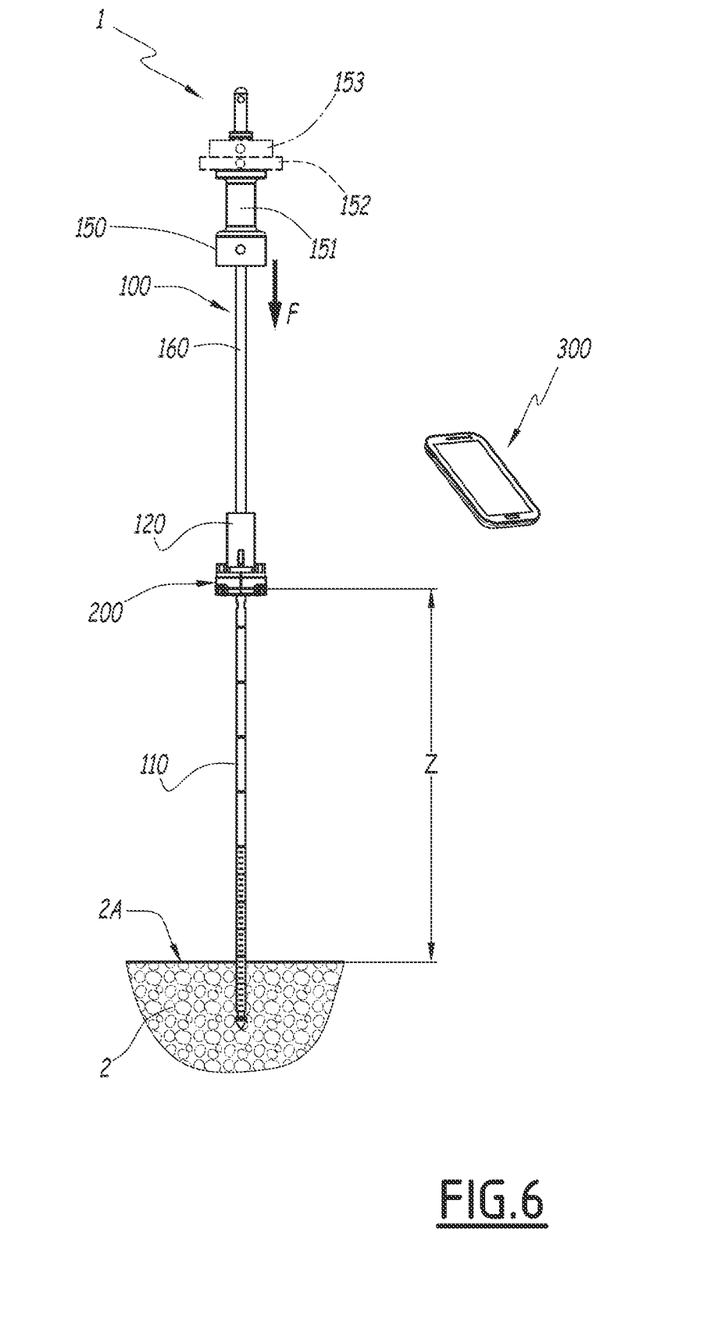
FIG. 6 is an elevation view of the measuring system of FIG. 1, in use.
Figure 7:
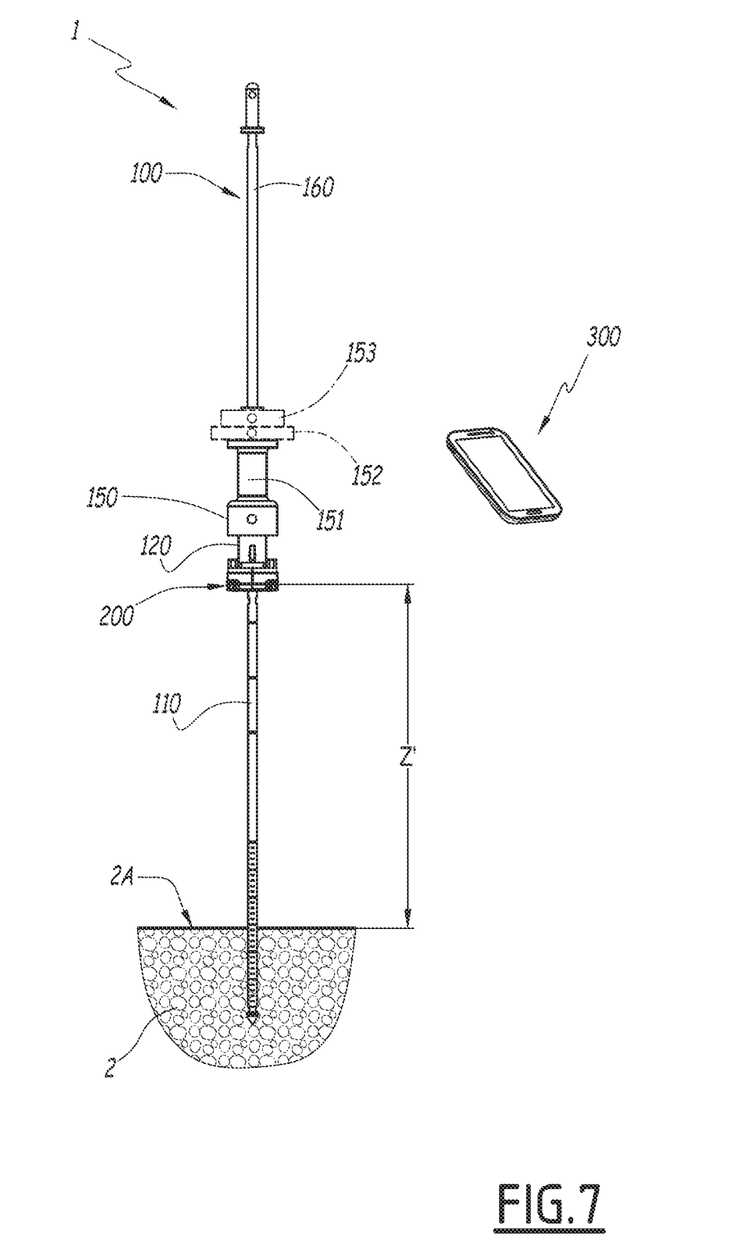
FIG. 7 is a view similar to FIG. 6, illustrating a step in the use of the measuring system, subsequent to that shown in FIG. 6.

As shown in FIGS. 1 to 3, 6 and 7, the measuring system 1 comprises a dynamic penetrometer 100. The dynamic penetrometer 100 defines a geometrical axis X-X, along which dynamic penetrometer 100 extends and which, when measuring system 1 is used, is arranged strictly vertical or slightly inclined with respect to it, as shown in FIGS. 6 and 7.

For convenience, the rest of the description is oriented with respect to the X-X axis, the latter considered to extend vertically. Thus, the terms "low", "lower" and "similar" are understood to be oriented towards the soil 2, while the terms "high", "upper" and "similar" are understood to be oriented away from the soil 2.

As clearly visible in FIGS. 1, 2, 6 and 7, the 100 dynamic penetrometer comprises a train of rods 110 that is aligned and centered on the X-X axis. At its lower end, the train of rods 110 includes a point 111 which, as in the example considered here, is conical, centered on the X-X axis and converges downwards. In a manner known per se, the cross-section and the opening angle of the point 111 are specific to the dynamic penetrometer 100, with this aspect not being limitative for the invention. Regardless of the specificities of the point 111, the latter allows the deformation and shearing of the soil 2 when an impact is applied downward along the X-X axis.

The remainder of the train of rods 110 comprises rods 112, which follow one another in a straight line along the X-X axis from the point 111 to the upper end of the train of rods 110, formed by the upper end portion of the highest of the rods 112. Again, the axial dimension and diameter of the rods 112 are specific to the dynamic penetrometer 100, this aspect not being limitative for the invention. In all cases, the rods 112 are designed to be mechanically connected to each other, for example by screwing or by fitting. The rods 112 make it possible to transmit an impact applied downwards along the X-X axis to the highest of the rods 111, thus allowing the train of rods 110 to be driven into the soil 2.

The dynamic penetrometer 100 also comprises an anvil 120, which is arranged axially plumb with the train of rods 110 and is designed to receive successive downward impacts along the X-X axis and transmit them to the train of rods 110. The form of construction of the anvil 120 is not limitative for the invention since, on its lower side, the anvil is designed to be mechanically connected to the upper end of the train of rods 110 and to transmit to the latter a downward impact along the X-X axis. In the embodiment considered in the Figures, the anvil 120 has an overall cylindrical shape, centered on the X-X axis.

Figure 2:
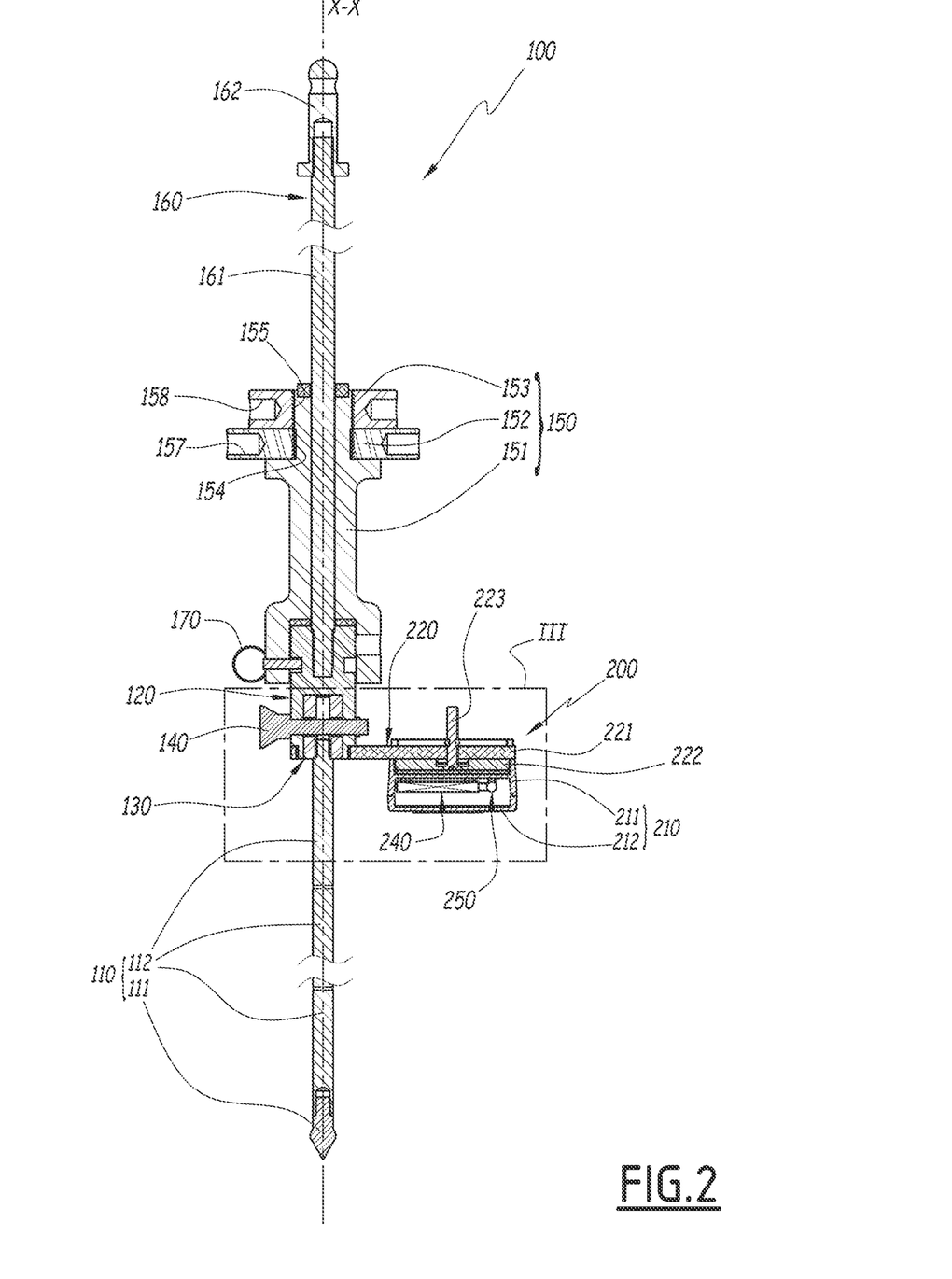
FIG. 2 is a longitudinal section of a penetrometer and a measuring device, assembled to each other, of the measuring system of FIG. 1.
Figure 3:
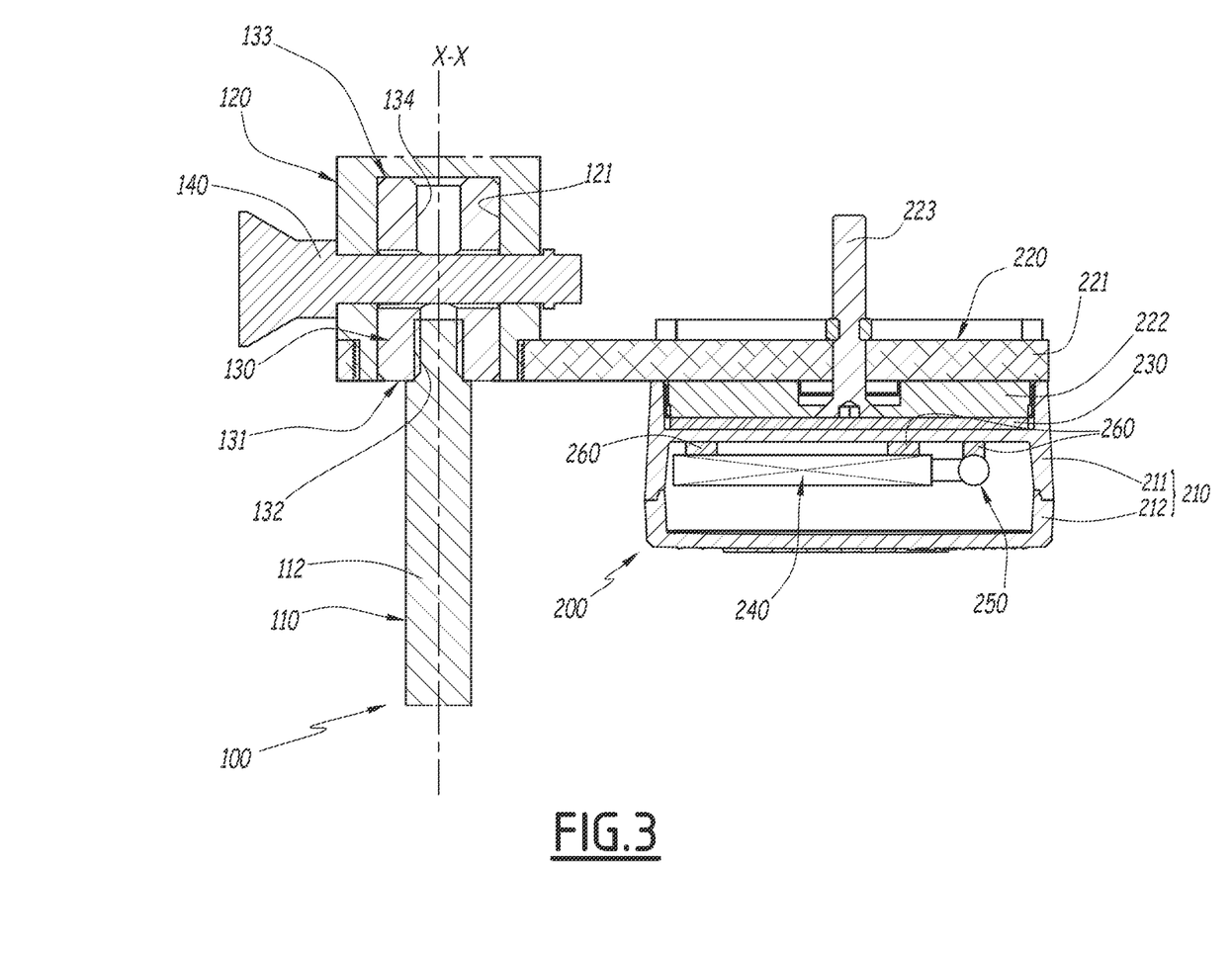
FIG. 3 is a larger scale view of detail III in FIG. 2.

The dynamic penetrometer 100 also comprises an adapter 130 which enables mechanically joining the anvil 120 and the train of rods 110. As seen in FIGS. 1 to 3, the adapter 130 is interposed, along the X-X axis, between the anvil 120 and the train of rods 110, bearing axially against both the anvil 120 and the train of rods 110, more precisely the highest rod 112 of the latter. In the embodiment considered in the Figures, the adapter 130 has a generally cylindrical shape, centered on the axis X-X, and is at least partially received in a complementary way in a housing 121 of the anvil 120, opening on the lower side of the anvil 120. In practice, a pin 140 is provided to retain the adapter 130 inside the recess 121 and thus prevent unintentional disassembly, this pin 140 extending across the anvil 120 and the adapter 130, especially in a direction radial to the X-X axis. On its opposite side, which is facing downwards in the Figures, the adapter 130 has both a face 131, which extends in a geometric plane perpendicular to the X-X axis, and a thread 132, which is centered on the X-X axis and opens onto the face 131. On its opposite side, that is, on its side facing upwards in the Figures, the adapter 130 has both a face 133, which extends in a geometric plane perpendicular to the X-X axis, and a bore 134, which is centered on the X-X axis and opens onto the face 133.

The thread 132 is designed to receive a complementary thread, by screwing, at the upper end of the train of rods 110 considered in the Figures: Thus, in the assembled state of the dynamic penetrometer 100 shown in the figures, the thread of the upper end of the train of rods 110 is screwed completely into the thread 132 until a shoulder at the base of this thread is axially supported against the face 131 of the adapter 130, while the face 133 of the adapter 130 forms a downward axial support for the anvil 120, in particular for the bottom of the housing 121. Thanks to its bore 134, the adapter 130 can be used within the dynamic penetrometer 100 in a different configuration from the one just described, when the upper end of the train of rods 110 has no thread but is made as a smooth cylindrical pin, not shown in the figures: when the upper end of the train of rods 110 is made of such a smooth cylindrical pin, the adapter 130 is used in a reversed position with respect to that shown in the Figures, that is, so that its face 133 is turned downwards and bore 134 receives the smooth cylindrical pin until a shoulder is axially supported, provided at the base of this nipple, against the face 133, while at the same time the face 131 of the adapter 130 forms an axial downward support for the anvil 120, especially for the bottom of the housing 121. Thus, the adapter 130 allows the use of the anvil 120 with two different types of rods trains, namely the train of rods 110 shown in the Figures, having its upper end threaded, and another train of rods, having a smooth cylindrical upper end.

The dynamic penetrometer 100 also comprises a hammer 150 which is movably mounted on a guide 160 attached to the anvil 120. In the example embodiment considered in the Figures, the hammer 150 has a tubular overall shape, which is centered on the X-X axis and whose central bore receives a bar 161 of the guide 160, extending upward from the anvil 120 and being integrally connected to the latter by any appropriate means. The hammer 150 is movable along the X-X axis along the bar 161 between a high position, which is shown in FIG. 6 and in which the hammer is spaced from the anvil 120, and a low position, which is shown in FIG. 7 and in which the hammer 150 is in contact with the anvil 120, so that the hammer 150 applies a downward impact along the X-X axis to the anvil 120 when it moves from the high position to the low position. In practice, when using the dynamic penetrometer 100, the hammer 150 is lifted to the high position, before being released so that, under the effect of gravity, it falls on the anvil 120. The upper position is marked on the guide 160 so that the distance between the anvil 120 and the hammer 150 in the upper position is predetermined at a value that remains fixed each time the hammer is lifted to this upper position: in the embodiment considered in the figures, this marking of the upper position is carried out by means of an object provided at the upper end of the guide 160, against which the hammer 150 in the upper position is brought into contact. This object is advantageously integrated into a handle 162 on top of the bar 161.

As clearly visible in FIGS. 1 and 2, the hammer 150 advantageously includes several separate hammer elements, at least one of which is removable relative to the rest of the hammer 150 and thus relative to the rest of the dynamic penetrometer 100.

More precisely, in the example embodiment considered in the Figures, the hammer 150 thus includes a first hammer element 151 which, in the hammer, interacts by complementarity of shapes with the guide 160 during the movement of the hammer between the upper and lower positions, in particular by sliding around and along the bar 161. The first hammer element 151 has a tubular shape, centered on the X-X axis.

The lower end of this first hammer element 151 is designed to be in contact with the anvil 120 when the hammer 150 is in the lower position, so as to be able to apply a downward impact along the X-X axis. The lower end of the first hammer element 151 is advantageously bell-shaped so as to internally receive at least a part of the anvil 120 when the hammer 150 is in the lower position: this bell shape makes it possible to attenuate the intensity of the noise generated during the impact of the hammer 150 on the anvil 120, by the effect of confining this noise inside the bell. According to another advantageous optional aspect that improves the ergonomics of the hammer 150, the current part of the first hammer element 151, that is the part that connects the lower and upper ends of the first hammer element 151 to each other, is shaped to make it easier to grip the first hammer element 151 and thus the hammer 150. In the embodiment considered in the Figures, this current part of the first hammer element 151 thus has a cylindrical shape with a circular cross-section whose diameter is smaller than the respective transverse dimensions of the lower and upper ends of the first hammer element 151. In addition, a pin 170, arranged across the lower end of the first hammer element 151 and across the part of the anvil 120, received in this lower end of the first hammer element 151, can be provided to hold the anvil 120 and the first hammer element 151 together when the hammer 150 is not used for the purpose of applying an impact on the anvil, for example during the transport and installation of the dynamic penetrometer 100.

The hammer 150 also includes a second hammer element 152 and a third hammer element 153 that are each designed to be removably attached to the first hammer element 151. For this purpose, each of the hammer elements 152 and 153 is provided with an internal thread 154, 155, which is centered on the X-X axis and which is intended to be screwed onto a complementary thread 156 of the first hammer element 151. In the example shown in the figures, the thread 156 is provided at the upper end of the first hammer element 151. In any case, each of the hammer elements 152 and 153 can thus be screwed directly onto the first hammer element 151, on the one hand without having to disassemble the first hammer element 151 from the guide 160 and, on the other hand, without the need for additional fastenings such as screws. Advantageously, in order to facilitate the rotational drive of each of the hammer elements 152 and 153 for the purpose of screwing and unscrewing them with respect to the thread 156, each of the hammer elements 152 and 153 is provided with at least one lateral hole 157, 158, which extends in a radial direction to the X-X axis and which is adapted to receive one of the two ends of a rod similar to the rods 112: in this way, in the field, an operator can use one of the rods 112, not yet used in the train of rods 110, to insert one end into the hole 157, 158 and thus more easily apply a screwing-unscrewing torque to the corresponding hammer element 152, 153 for the purpose of assembling or disassembling this hammer element 152, 153 with respect to the first hammer element 151.

Regardless of the specifics of the hammer elements 151, 152 and 153 of the hammer 150, it is understood that the weight of the hammer 150 changes according to the actual presence of one and/or the other of the hammer elements 152 and 153, in addition to the systematic presence of the first hammer element 151 in the hammer 150.

Figure 4:
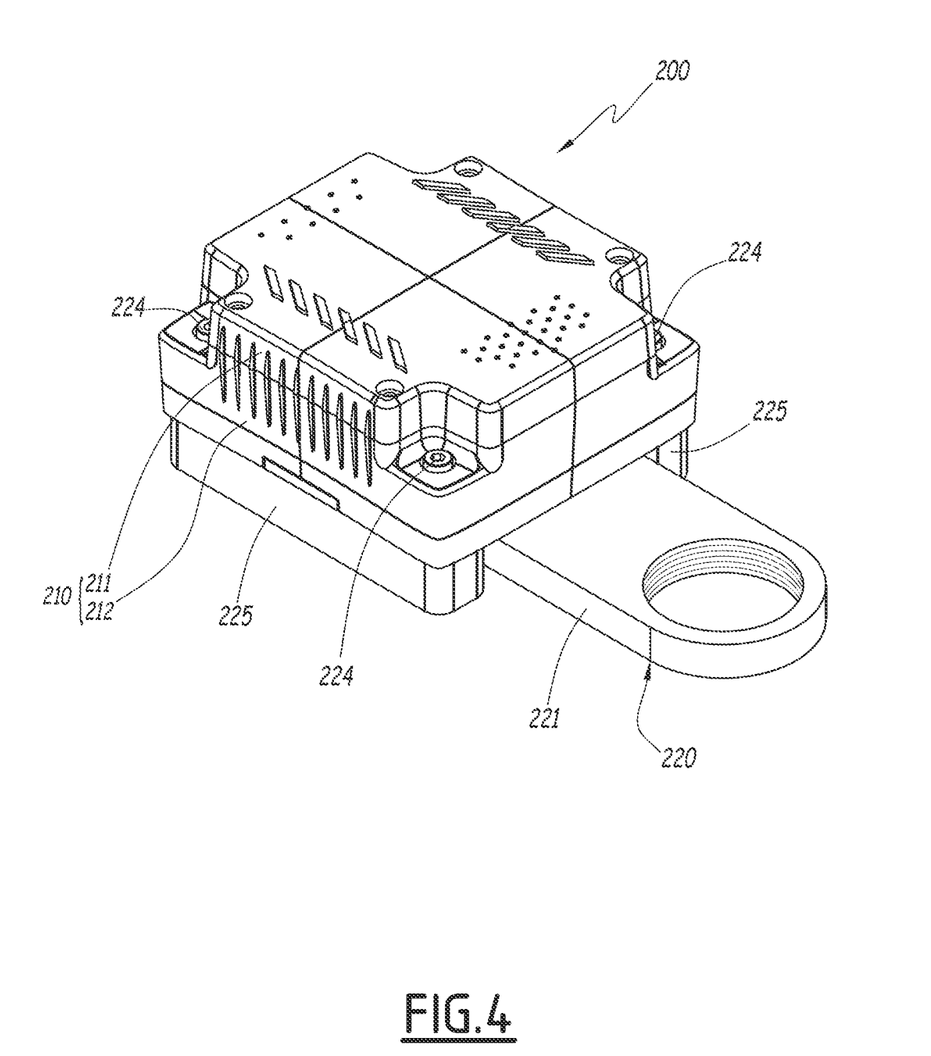
FIG. 4 is a perspective view of the measuring device shown in the previous Figures.
Figure 5:
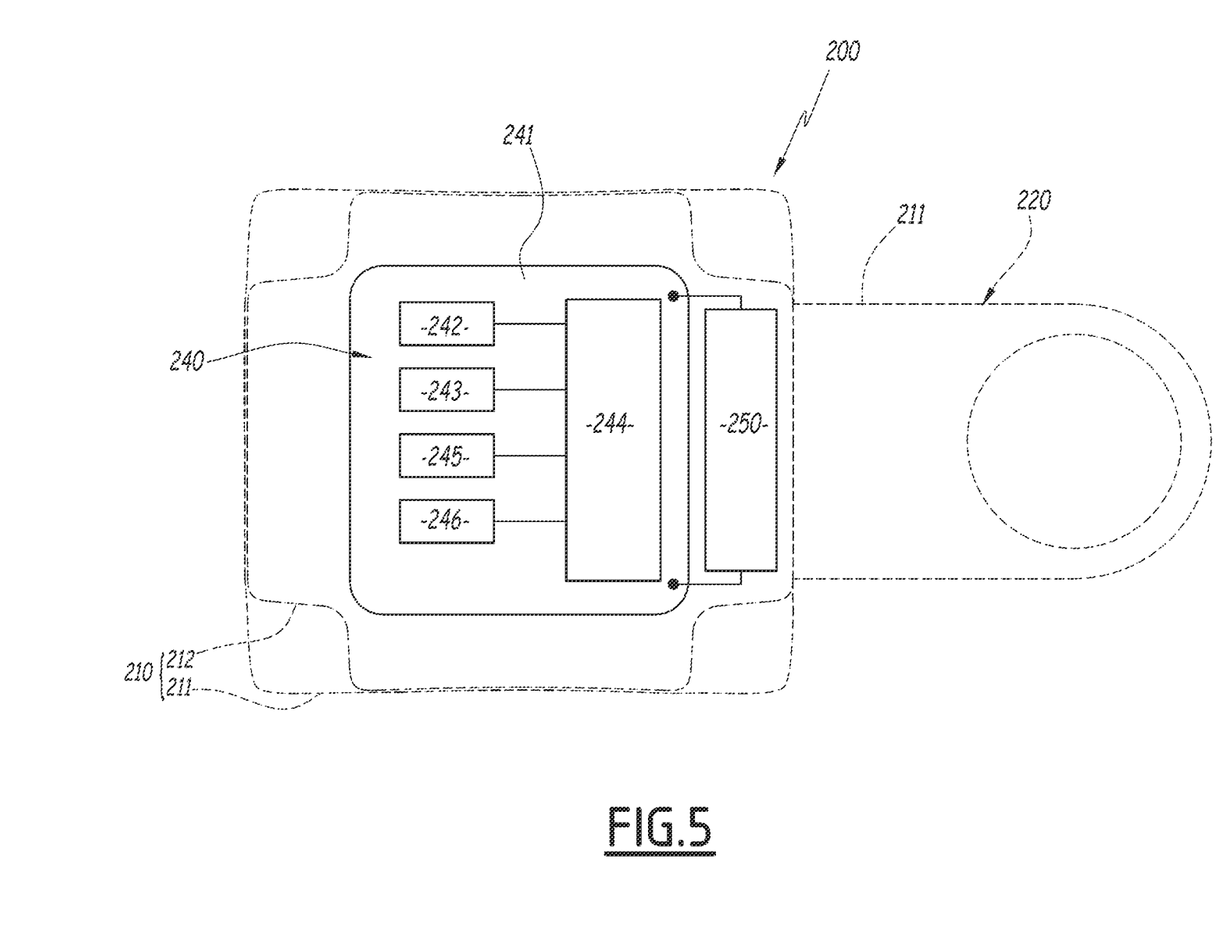
FIG. 5 is an elevation view according to arrow V in FIG. 4, schematically showing the outer contour of the measuring device and the inside of a housing of the measuring device.

As clearly visible in FIGS. 1 to 3, the measuring system 1 comprises, in addition to the dynamic penetrometer 100 described so far, a measuring device 200, which is shown alone in FIGS. 4 and 5.

The measuring device 200 has a housing 210 which, in the example of the design considered in the Figures, includes a main shell 211 and a cover 212. In practice, the housing 210 is advantageously made of a plastic material, while being designed to withstand shocks and, more generally, outdoor conditions of use in the field to be evaluated.

The housing 210 is adapted to be secured, in particular in a removable way, to the dynamic penetrometer 100. For this purpose, in the embodiment considered on the figures, the measuring device 200 comprises a means of mechanical fastening 220 whose embodiment, considered in the example of the figures, is detailed just below.

The means of mechanical fastening 220 comprises a plate 221, in particular a metal plate 221, which extends transversely to the axis X-X. At its end facing the X-X axis, the plate 221 is mechanically secured to the dynamic penetrometer, interacting directly with the latter. In the example considered in the figures, the plate 221 is thus provided with an internal thread which, for the purpose of joining it to the dynamic penetrometer 100, is screwed around a complementary thread of the anvil 120.

At its end opposite to the X-X axis, the plate 221 is mechanically secured to the housing 210. For this purpose, in the example embodiment considered in the Figures, the means of mechanical fastening 220 comprise a base plate 222, in particular metallic, which, on the one hand, is mechanically connected to plate 221 by a bolt 223 and, on the other hand, is connected to the main shell 211 of the case 10 by screws 224. To reinforce the fixed assembly between the plate 221 and base plate 222, the means of mechanical fastening 220 also include shims 225, which are arranged along and on either side of the plate 221 and are connected to the base plate 222 by screws 224.

The embodiment of the means of mechanical fastening 220, which has just been described, is not limitative for the invention, in the sense that multiple embodiments can be envisaged for the means of mechanical fastening 220 as long as the latter secure the housing 210 to the dynamic penetrometer 100, in particular to its anvil 120, by a reversible mechanical connection.

Whatever the form of achieving the means of mechanical fastening 220, the measuring device 200 advantageously comprises at least one damper 230, typically made of rubber or a similar elastomeric material, which is interposed between the housing 210 and the means of mechanical fastening 220 so as to limit the transmission to the housing 210 of vibrations coming from the dynamic penetrometer 100. In the embodiment considered in the Figures, the damper 230 is interposed between the housing 210 and the base plate 222, as shown schematically in FIG. 3.

As more specifically shown in FIGS. 3 and 5, the measuring device 200 also comprises an electronic system 240.

This electronic system 240 is accommodated inside the housing 210, notably being received in an internal volume of this housing, delimited by the main shell 211 and the cover 212. In practice, this internal volume of the housing 210 is sealed from the outside of the housing 210 by any appropriate means integrated into the housing 210, so as to protect the electronic system 240 from water and humidity.

As shown schematically in FIG. 5, the electronic system 240 comprises several components or groups of components, which will be detailed below and which are advantageously held on a common electronic card 241.

The electronic system 240 thus comprises an accelerometer 242 that is capable of measuring the acceleration of the electronic system 240 and thus of the measuring device 200. The specific features of the accelerometer 242 are not limiting the invention.

The electronic system 240 also comprises a distance sensor 243 capable of determining the distance from a surface to which the distance sensor 243 is directed. For this purpose, the distance sensor 243 is designed to measure the time required for a wave, which it emits, to travel back and forth between itself and the surface to which it is directed. In practice, the above-mentioned wave is a light wave, for example in the infrared range, or a sound wave. In any case, the distance sensor 243 incorporates both a transmitter capable of emitting this wave and a receiver capable of detecting the wave returning to the distance sensor 243 after having been reflected, at least partially, by the surface to which the distance sensor 243 is directed. Thus, the distance sensor 243 is commonly referred to as a "TOF" distance sensor ("TOF" stands for Time Of Flight). When the housing 210 is secured to the penetrometer 100 and the measuring system 1 is in use, the distance sensor 243 is oriented towards the soil 2 to be evaluated, so that the distance sensor 243 can determine the distance between the measuring device 200 and the surface 2A of the soil 2. It is understandable that the arrangement of the distance sensor 243 inside the housing 210 and the arrangement of the measuring device 200 on the dynamic penetrometer 100 are provided accordingly, that is, are designed so that the distance sensor 243 is oriented towards soil 2 when using the measuring system 1. In the embodiment example shown in the Figures, the distance sensor 243 is oriented towards the cover 212 of the housing 210 and, when the measuring system 1 is used as in FIGS. 6 and 7, the cover 212 is oriented towards the surface 2A of the soil 2. Of course, the cover 212 is made of a material that allows the wave emitted by the distance sensor 243 to pass through.

The electronic system 240 also comprises a processing unit 244 which, as shown schematically in FIG. 5, is connected to the accelerometer 242 and the distance sensor 243. The processing unit 244 is thus designed to receive the measuring signals from the accelerometer 242 and the distance sensor 243 respectively. The processing unit 244 is adapted to apply a first processing to these measuring signals, it being noted that the specificities relating to this first processing will be given later. In practice, the processing unit 244 comprises both analog and digital electronic components, in order to implement the first processing mentioned above.

According to optional provisions, whose interest will appear later, the electronic system 240 also comprises:

a wireless communication interface 245 capable of transmitting to the outside of the measuring device 200, according to a wireless communication protocol, the data resulting from the first processing applied by the processing unit 244, the above-mentioned protocol being advantageously low-power; this wireless communication interface 245 is, for example, a Wi-Fi interface or a Bluetooth interface, particularly a low-power interface commonly known as the "BLE" interface (acronym for "Bluetooth Low Energy");

a tilt sensor 246 capable of measuring the tilt of the measuring device 200 with respect to the vertical; the tilt sensor 246 is for example an electronic gyroscope; and one or more other sensors that are sensitive to the conditions of use of the measuring device 200, such as a temperature sensor, a brightness sensor, a location sensor, etc.

Of course, the wireless communication interface 245, the tilt sensor 246 and any other sensors are connected to the processing unit 244, as shown schematically in FIG. 5, for the processing of their respective signals by this processing unit.

The measuring device 200 also comprises a power supply battery 250, which is accommodated inside the housing 210 and which, as shown schematically in FIG. 5, is connected to the electronic system 240 in order to supply power to the various components of this electronic system 240. The power supply battery 250 is, for example, connected to the electronic card 241. The embodiment of this power supply battery 250 is not limitative for the invention.

As shown schematically in FIG. 3, the measuring device 200 also comprises dampers 260, which are interposed between the housing 210 and the electronic system 240, in particular the electronic card 241 of the latter, as well as, if necessary, between the housing 210 and the power supply battery 250. These dampers 260 make it possible to limit the exposure of the electronic system 240 and the power supply battery 250 to the vibrations coming from the dynamic penetrometer 100 when using the measuring system 1. The viewing time of the electronic system 240 and the power supply battery 250 is thus not altered, despite the fact that the housing 210 is attached to the dynamic penetrometer 100, which is the site of repeated impacts during the use of the measuring system 1.

Finally, the measuring system 1 comprises a processing device 300, as shown in FIGS. 1, 6 and 7. This processing device 300 is distinct from the dynamic penetrometer 100 and the measuring device 200, being physically separate from the dynamic penetrometer 100 and the measuring device 200.

The processing device 300 is adapted to apply a second processing to the data resulting from the first processing applied by the processing unit 244 to the measuring signals coming from the accelerometer 242 and the distance sensor 243, as well as from the tilt sensor 246, if applicable, and any other sensors of the electronic system 240. The specifics relating to this second processing will be provided a little later.

In any case, the processing device 300 is designed to receive the data resulting from the first processing applied by the processing unit 244. In the example embodiment considered in the figures, the processing device 300 includes a wireless communication interface for this purpose, which is compatible with the wireless communication interface 245 of the electronic system 240. More generally, the electronic system 240 of the measuring device 200 and the processing device 300 are designed to exchange data wirelessly via an ad hoc communication protocol as shown in the figures, or via a wired link, such as a USB, or a removable memory medium, such as a memory card.

The processing device 300 comprises digital electronic components that enable the above-mentioned second processing to be implemented. The embodiment of these digital electronic components is not limitative for the invention. As an example, the processing device 300 contains, or even consists of, a mobile terminal, such as a laptop computer, a tablet or an intelligent cell phone, or a computer platform.

We will now describe a measuring method, which is implemented with the measuring system 1 and through which the first and second treatments respectively applied by the processing unit 244 of the measuring device 200 and by the processing device 300 will be presented in more detail. This measuring method is described more specifically in connection with FIGS. 6 and 7 on which the measuring system 1 is in use on the soil 2.

In FIG. 6, the train of rods 110 of the penetrometer 100 is already partially embedded in the soil 2, with the tip 111 being located below the surface 2A of the soil 2. This partial boring is the result of impacts that were applied to the anvil 120 by the hammer 150 prior to the use stage shown in FIG. 6. As already mentioned above, to apply an impact to the anvil 120, the hammer 150 is moved away from the anvil 120 by being lifted to the high position, advantageously marked by the handle 162, then the hammer 150 is released so that it falls on the anvil 120, thus passing to the low position.

At the end of the last impact before the step illustrated in FIG. 6, the interval between the distance sensor 243 and the surface 2A of the soil 2 is determined using distance the sensor 243, which measures the time required for the wave it emits to travel back and forth between it and the surface 2A of the soil 2. The above-mentioned interval corresponds to a distance, denoted Z in FIG. 6, between the measuring device 200 and the surface 2A of the soil 2.

At the step shown in FIG. 6, the hammer 150 is in the up position and is released to move to the down position, as indicated by the arrow F. When the hammer 150 actually reaches the low position, it applies an impact on the anvil 120 which transmits it to the train of rods 110, this train of rods 110 then boring further into the soil 2: the measuring system 1 is then in the state shown in FIG. 7.

When the impact is applied to the anvil 120 to move from FIG. 6 to FIG. 7, the anvil 120 and, consequently, the measuring device 200 secured to it undergo a substantial acceleration, that is, a strong amplitude, typically of several g. This acceleration is measured using the accelerometer 242. The corresponding impact is detected from the acceleration thus measured, in particular from a peak amplitude of this measured acceleration.

At the end of the impact applied to pass from FIG. 6 to FIG. 7, the distance, denoted Z' in FIG. 7, between the measuring device 200 and the surface 2A of the soil 2 is measured using the distance sensor 243, in the same way as the distance Z was previously measured. The boring of the train of rods 110 into the soil 2 between the states respectively illustrated by FIGS. 6 and 7 is then determined from the measured distances Z and Z', this boring corresponding to the difference between the distance Z and the distance Z'.

It is understood that by successively repeating impacts on the anvil 120 using the hammer 150, these different successive impacts are individually detected from the accelerations measured by the accelerometer 242. The number of these impacts can thus be counted. At the same time, the progressive boring of the train of rods 110 is determined after each of these impacts from the distances measured by the distance sensor 243.

Numerical data showing the number of successively applied impacts and the boring of train of rods 110 at the end of each impact allow the calculation of the geomechanical characteristics of the soil 2, in particular the resistance values of the soil 2. For example, a penetration index for the soil 2 can thus be calculated, in particular from the Dutch ramming formula or other formulas known in literature.

In practice, the digital data mentioned just above is provided either exclusively by the processing unit 244, via the first processing it applies to the measuring signals coming from the accelerometer 242 and the distance sensor 243, or jointly by the processing unit 244 and the processing device 300, successively via the first processing, which the processing unit 244 applies to the measuring signals coming from the accelerometer 242 and the distance sensor 243, and the second processing, which the processing device 300 applies to the data resulting from the first processing.

In other words, according to a first embodiment option of the measuring system 1, the processing unit 244 is adapted, via the first processing, to detect the different successive impacts from the measuring signals coming from the accelerometer 242 and to determine the boring of the train of rods 110 in the soil 2 at the end of each step from the measuring signals coming from the distance sensor 243. In this case, the processing device 300 does not intervene to provide the digital data showing the number of impacts and the progressive boring of the train of rods 110, but this processing device 300 is, if necessary, used to consult these data and/or store them and/or transmit them to remote servers, in particular for post-processing purposes that are more sophisticated than the first processing applied by the processing unit 244.

According to another embodiment option of the measuring system 1, the processing unit 244 and the processing device 300 are jointly adapted, via the first and second processing, to detect the different successive impacts from the measuring signals coming from the accelerometer 242 and to determine the boring of the train of rods 110 into the soil 2 at the end of each impact from the measuring signals coming from the distance sensor 243. In this case, the first processing, carried out by the processing unit 244, can simply be analog-to-digital conversion, converting the measuring signals into data that can be used for the second processing, carried out by the processing device 300. More generally, it is understood that the evaluation of the measuring signals coming from accelerometer 242 and distance sensor 243 can be limited to the processing unit 244 via the first processing, provided that the processing device 300 is intended to complete this evaluation via the second processing: in this case, the processing unit 244 can be reduced to a minimal embodiment. Conversely, if the processing capacities of the processing device 300 are limited or uncertain, a substantial part of this operation can be provided by processing unit 244, via the first processing.

Thus, in all cases, the measuring signals coming from the accelerometer 242 and the measuring signals coming from the distance sensor 243 are processed at least by the processing unit 244.

Of course, what has just been described in detail for the measuring signals coming from the accelerometer 242 and the distance sensor 243 applies to the measuring signals coming from the tilt sensor 246 and any other sensors of the electronic system 240. In particular, the data obtained from the measuring signals coming from the tilt sensor 246 can then be stored for control purposes.

As an optional aspect of the measuring method, the acceleration measured at each impact is advantageously used to determine which of the hammer elements 151, 152 and 153 of the hammer element 150 is or are actually present in the hammer that was used to apply the impact. Indeed, it should be noted that in the steps of use illustrated in FIGS. 6 and 7, as well as in each of the earlier and later steps of use, the hammer 150 can be used with only the hammer element 151 or with the hammer element 151 and either or both of hammer elements 152 and 153, as shown schematically in the dotted and mixed lines in FIGS. 6 and 7. For this purpose, either exclusively the first processing, or successively the first and second processing are provided to evaluate the measuring signals coming from the accelerometer 242 in order to determine whether, in addition to the first hammer element 151 systematically present in the hammer 50, one and/or the other of the hammer elements 152 and 153 are present in the hammer 150. This calculation is carried out using a transfer function that relates, by means of a prior calibration of the measuring system 1, the effective mass of the hammer 150 and the acceleration measured by the accelerometer 242. In other words, during each impact, the processing unit 244 or the processing unit 244 and the processing device 300 are able to detect which of the hammer elements 151, 152 and 153 are actually present in the hammer 150. By adding or removing the hammer elements 152 and 153 to the hammer 150, the user can therefore easily change the weight of the hammer 150 during boring, in particular to adapt to the layers of soil encountered during boring, without having to worry about recording this information since the measuring system 1 determines this information by itself from the measuring signals coming from the accelerometer 242, it being emphasized that this information is decisive for calculating certain geomechanical characteristics of the soil.

According to another optional aspect relating to the exploitation of the measuring signals coming from the accelerometer 242, the energy autonomy of the measuring device 200 can be substantially improved. For this purpose, the electronic system 240 is advantageously designed to switch between an operating state, in which the power supply battery 250 powers the entire electronic system 240, thus enabling the method described so far, and a standby state, in which the processing unit 244 interrupts the power supply from the power supply battery 250 to the distance sensor 243 and, advantageously, to all other components of the electronic system 240 except the accelerometer 242 and the processing unit itself. The processing unit 244 is then adapted, on the one hand, to switch the electronic system from the standby state to the operating state when the amplitude of the acceleration measured by the accelerometer 242 exceeds a predetermined threshold, for example, approximately 1 g, and, on the other hand, to switch from the operating state to the standby state when the amplitude of the acceleration measured by the accelerometer 242 remains below the aforementioned threshold for a predetermined period of time, e.g. 5 minutes. The result is that, apart from boring, the electronic system 240 is in standby and therefore consumes very little power, preserving the power supply battery 250. During a boring, the operator "awakens" the electronic system 240, that is, makes it go from the standby state to the operating state, by subjecting it to a sufficiently strong acceleration, which, in practice, corresponds to a shock that the operator applies either directly to the measuring device 200 by hand, or to the penetrometer 200, in particular using the hammer 150. During the probing process, the successive impacts of the hammer 150 on the anvil 120 "keep awake" the electronic system 240, that is, the electronic system 240 remains in working order. After the boring process has been completed, the electronic system 240 remains in the operating state for the aforementioned predetermined time, after which the processing unit 244 switches electronic system 240 to the standby state. Thus, during the storage and transport of the measuring device 200, as well as during the assembly of the measuring device 200 on the dynamic penetrometer 100, the electronic system 240 remains in the standby state, it being understood that the accelerations experienced by the measuring device 200 during these storage, transport and assembly operations are insufficient in amplitude to switch the electronic system 240 into the operating state.

In addition, various modifications and variants of the measuring system 1 described so far, as well as of the measuring method described above, can be considered. The following are examples, which can be considered separately or in combination with each other:

- In addition to or instead of the means of mechanical fastening 220, the measuring device 200 can include magnetic means of fastening allowing the housing 210 to be secured to the dynamic penetrometer 100 by a magnetic connection. For example, the housing 210 is then equipped with one or more permanent magnets which, by magnetic effect with a steel part of the dynamic penetrometer 100, are firmly attached to the latter.
- As mentioned above, the region of the dynamic penetrometer 100 to which the measuring device 200 is fixedly attached is not limited to the anvil 120. Indeed, by adapting the means of mechanical fastening 220 or the means of magnetic fastening, mentioned just above, the housing 210 can be provided to be secured to the train of rods 110 or to the guide 160, or even to the hammer 150. More generally, the location of the measuring device 200 on the dynamic penetrometer 100 is not limiting as long as this location allows to induce a substantial acceleration of the measuring device 200 when an impact is applied to the anvil 120 by the hammer 150.
- In the example considered in the figures, the dynamic penetrometer 100 can be qualified as a light dynamic penetrometer in the sense that hammer 150 can be sized to be manually lifted from its low to high position by a human operator. However, as an alternative, not shown, the dynamic penetrometer of the measuring system 1 may be a heavier dynamic penetrometer, in particular having a hammer with a higher weight and whose lifting requires special equipment. More generally, the measuring device 200 can be related to various types of dynamic penetrometers.

The number of hammer elements of the hammer 150, at least one of which is removable in relation to the rest of the hammer, is not limited to three as in the example shown in the figures. Thus, as an alternative not shown, the hammer 150 may have only two hammer elements or more than three hammer elements. In any case, the or each hammer element of the hammer, which is removable relative to the rest of the dynamic penetrometer, is advantageously screwed directly onto another hammer element of the hammer, as is the case for each of the hammer elements 152 and 153 relative to the hammer element 151.

As an alternative not shown, the dynamic penetrometer 100 can be without an adapter such as the adapter 130 described above. In this case, the upper end of the train of rods 110 cooperates directly with the lower side of the anvil 120.

The invention claimed is:

1. A measuring device for geomechanical characterization of a soil, comprising:
   a housing, adapted to be secured to a dynamic penetrometer;
   a power supply battery, which is accommodated in the housing; and
   an electronic system, which is accommodated in the housing, and is connected to the power supply battery, said electronic system comprising:
   an accelerometer adapted to measure an acceleration of the measuring device,
   a distance sensor, which is oriented towards a soil when the housing is secured to the dynamic penetrometer and which is adapted to determine a distance between the measuring device and a surface of the soil by measuring a time required for a wave emitted by the distance sensor to travel back and forth between the distance sensor and the surface of the soil, and
   a processing unit, which is connected to the accelerometer and the distance sensor and which, when the electronic system is in an operating state in which the power supply battery powers entirely the electronic system, is adapted to apply a first processing to measuring signals coming from the accelerometer and the distance sensor.

2. The measuring device according to claim 1, wherein the measuring device further comprises a magnetic fastening adapted to secure the housing to the dynamic penetrometer.

3. The measuring device according to claim 1, wherein the processing unit is also adapted to:
   switch the electronic system from a standby state, in which the processing unit interrupts the power supply to the distance sensor by the power supply battery, to the operating state when an amplitude of the acceleration measured by the accelerometer exceeds a predetermined threshold, and
   switch the electronic system from the operating state to the standby state when the amplitude of the acceleration measured by the accelerometer remains below said threshold for a predetermined time.

4. The measuring device according to claim 1, further comprising:
   at least one damper, which is interposed between the housing and the dynamic penetrometer when the housing is secured to the dynamic penetrometer and/or which is interposed between the housing and the electronic system.

5. The measuring device according to claim 1, further comprising:
   a mechanical fastening adapted to removably secure the housing to the dynamic penetrometer.

6. The measuring device according to claim 1, wherein the electronic system also comprises a tilt sensor, which is connected to the processing unit and which is adapted to measure a tilt of the measuring device relative to the vertical.

7. A measuring system for geomechanical characterization of a soil, comprising:
   a dynamic penetrometer, which includes a train of rods configured to be driven into the soil, and an anvil configured to receive successive impacts and transmit said successive impacts to the train of rods; and
   a measuring device, secured to the dynamic penetrometer, where said measuring device comprises
   a housing, adapted to be secured to a dynamic penetrometer,
   a power supply battery, which is accommodated in the housing, and
   an electronic system, which is accommodated in the housing, and is connected to the power supply battery, said electronic system comprising
   an accelerometer adapted to measure an acceleration of the measuring device,
   a distance sensor, which is oriented towards a soil when the housing is secured to the dynamic penetrometer and which is adapted to determine a distance between the measuring device and a surface of the soil by measuring a time required for a wave emitted by the distance sensor to travel back and forth between the distance sensor and the surface of the soil, and
   a processing unit, which is connected to the accelerometer and the distance sensor and which, when the electronic system is in an operating state in which the power supply battery powers entirely the electronic system, is adapted to apply a first processing to measuring signals coming from the accelerometer and the distance sensor.

8. The measuring system according to claim 7, wherein the processing unit of the measuring device is adapted, via the first processing, to detect individually the successive impacts from the measuring signals coming from the accelerometer and to determine boring of the train of rods into the soil after each impact from the measuring signals from the distance sensor.

9. The measuring system according to claim 7,
   wherein the measuring device further comprises a processing device, which is separate from the dynamic penetrometer and the measuring device and which is adapted to apply a second processing to data which result from the first processing applied by the processing unit of the measuring device to measuring signals from the accelerometer and the distance sensor during impacts, and
   wherein the processing unit and the processing device are adapted, via the first and second processes, to detect individually the successive impacts coming from the measuring signals coming from the accelerometer and to determine boring of the train of rods into the soil after each impact from the measuring signals coming from the distance sensor.

10. The measuring system according to claim 7, wherein the dynamic penetrometer also comprises a hammer that:
    is movably mounted on a guide attached to the anvil between a high position, in which the hammer is moved away from the anvil, and a low position, in which the hammer is in contact with the anvil, so that the hammer applies an impact to the anvil when the hammer passes from the high position to the low position, and
    includes several separate hammer elements, at least one of which is removable from the rest of the dynamic penetrometer,
    and wherein either the processing unit of the measuring device or the processing unit and the processing device are adapted, via, respectively, either the first treatment or the first and second treatments, to determine which of said hammer elements is or are actually present in the hammer at each impact, from the measuring signals coming from the accelerometer.

11. The measuring system according to claim 10, wherein the or each hammer element of the hammer, which is removable relative to the rest of the dynamic penetrometer, is screwable directly onto another hammer element of the hammer.

12. The system device according to claim 7, wherein the dynamic penetrometer has a mechanical connection adapter between the anvil and the train of rods, whose mechanical connection adapter has:
    on a first side, a first bearing face for the anvil and an internal thread for receiving a threaded end of the train of rods, the internal thread opening to the first bearing face, and
    on a second side opposite the first side, a second bearing face for the anvil and a bore for receiving a smooth cylindrical end of the train of rods, the bore opening onto the second bearing face.

13. A measuring method for the geomechanical characterization of a soil, comprising:
    providing a dynamic penetrometer, comprising a train of rods, designed to be driven into the soil, and an anvil, designed to receive successive impacts and transmit said successive impacts to the train of rods;
    providing a measuring device, secured to the dynamic penetrometer, the measuring device comprising
    a housing, adapted to be secured to a dynamic penetrometer,
    a power supply battery, which is accommodated in the housing, and
    an electronic system, which is accommodated in the housing, and is connected to the power supply battery, said electronic system comprising
       an accelerometer adapted to measure an acceleration of the measuring device,
       a distance sensor, which is oriented towards a soil when the housing is secured to the dynamic penetrometer and which is adapted to determine a distance between the measuring device and a surface of the soil by measuring a time required for a wave emitted by the distance sensor to travel back and forth between the distance sensor and the surface of the soil, and
       a processing unit, which is connected to the accelerometer and the distance sensor and which, when the electronic system is in an operating state in which the power supply battery powers entirely the electronic system, is adapted to apply a first processing to measuring signals coming from the accelerometer and the distance sensor;
    measuring an acceleration of the measuring device upon each impact, using the accelerometer;
    detecting individually the successive impacts from the measured accelerations, by processing the successive impacts by the processing unit;
    measuring a distance between the measuring device and the soil after each impact, using the distance sensor; and
    determining boring of the train of rods into the soil after each impact from the measured distances, by processing each impact with the processing unit.

14. The measuring method according to claim 13, wherein the dynamic penetrometer further comprises a hammer which:
    is movably mounted on a guide attached to the anvil,
    is configured to apply each impact to the anvil by raising the hammer to a predetermined height from the anvil and then releasing the hammer to fall on the anvil, and
    includes several separate hammer elements, at least one of which is removable from the rest of the dynamic penetrometer, and
    wherein the measuring method also comprises a step of determining which of said hammer elements is or are actually present in the hammer at each impact, from the measured acceleration upon the impact.

* * * * *